(12) United States Patent
Weyl et al.

(10) Patent No.: US 7,124,622 B2
(45) Date of Patent: Oct. 24, 2006

(54) SENSING ELEMENT FOR DETERMINING A PHYSICAL PROPERTY OF A GAS MIXTURE

(75) Inventors: Helmut Weyl, Wiesbaden (DE); Rainer Maier, Tamm (DE)

(73) Assignee: Robert Bosch GmbH, Stuttgart (DE)

(*) Notice: Subject to any disclaimer, the term of this patent is extended or adjusted under 35 U.S.C. 154(b) by 0 days.

(21) Appl. No.: 10/958,051

(22) Filed: Oct. 4, 2004

(65) Prior Publication Data

US 2005/0109077 A1    May 26, 2005

(30) Foreign Application Priority Data

Oct. 2, 2003   (DE) ................ 103 45 944

(51) Int. Cl.
*G01N 33/497* (2006.01)
*G01N 7/00* (2006.01)
*G01N 27/407* (2006.01)

(52) U.S. Cl. ............... 73/23.31; 73/31.05; 204/424

(58) Field of Classification Search ............... 73/23.31, 73/23.32, 31.05; 204/424, 425, 426, 427, 204/428, 429
See application file for complete search history.

(56) References Cited

U.S. PATENT DOCUMENTS

| | | | | |
|---|---|---|---|---|
| 4,219,399 A * | 8/1980 | Gruner et al. | ............... | 204/408 |
| 4,377,801 A * | 3/1983 | Weber et al. | ............... | 338/34 |
| 4,668,477 A * | 5/1987 | Nishio et al. | ............... | 422/98 |
| 6,478,941 B1 * | 11/2002 | E et al. | ............... | 204/427 |
| 6,497,808 B1 * | 12/2002 | Yamauchi et al. | ............... | 205/785 |
| 6,500,322 B1 * | 12/2002 | Akatsuka et al. | ............... | 204/427 |
| 2004/0035700 A1 * | 2/2004 | Taguchi et al. | ............... | 204/429 |

FOREIGN PATENT DOCUMENTS

DE    41 26 378    4/1992
DE    197 03 458    7/1997

* cited by examiner

*Primary Examiner*—Michael Cygan
(74) *Attorney, Agent, or Firm*—Kenyon & Kenyon LLP

(57) ABSTRACT

A sensing element for determining a physical property of a gas mixture, in particular the exhaust gas of internal combustion engines, includes a sensor element, arranged in a housing and connected to at least one electrical cable, as well as a molded piece, which seals the housing and is made of an elastically deformable material, which encloses the at least one cable in a gas-tight manner by radial compression. To ensure the gas-tightness of the cable feed-through also under a higher temperature load, which results in decreased elasticity of the molded piece, a spring element is arranged inside the molded piece, which is able to be tensioned by the radial compression and in the tensioned state generates a force component that acts on the cables in a radial direction.

16 Claims, 4 Drawing Sheets

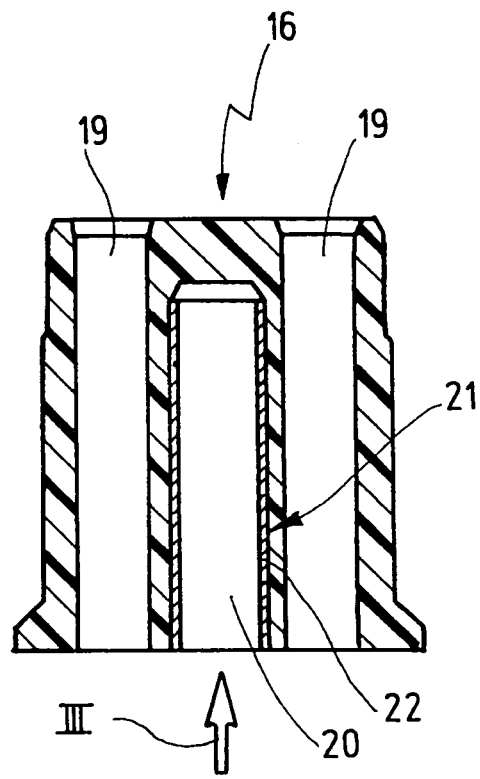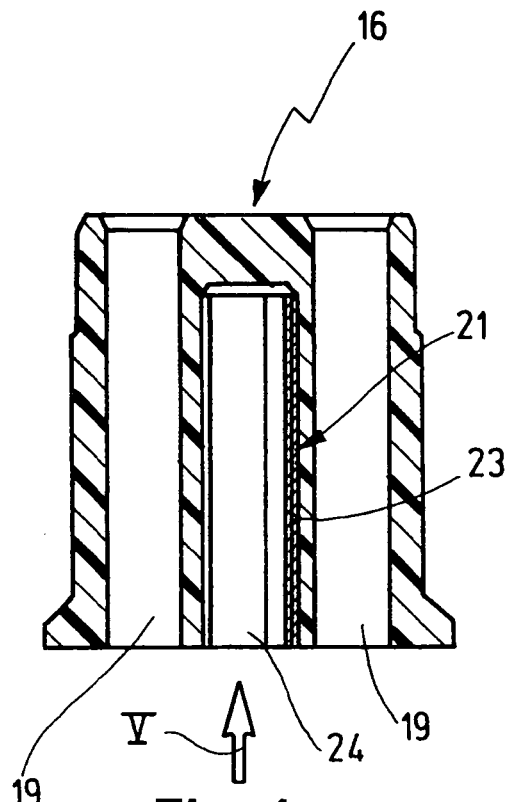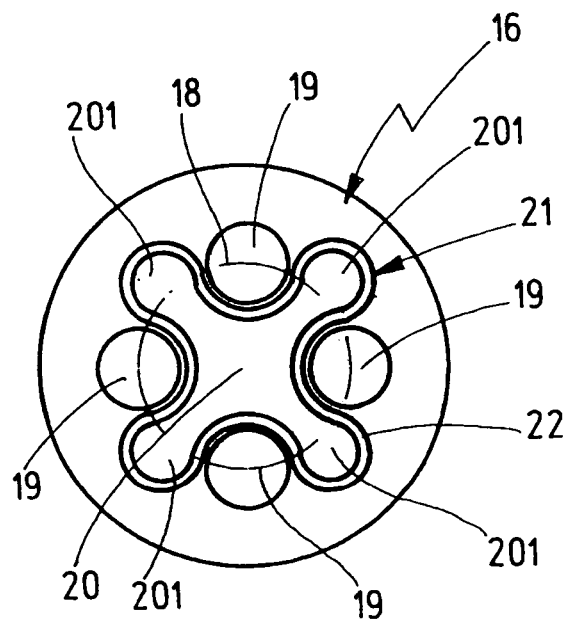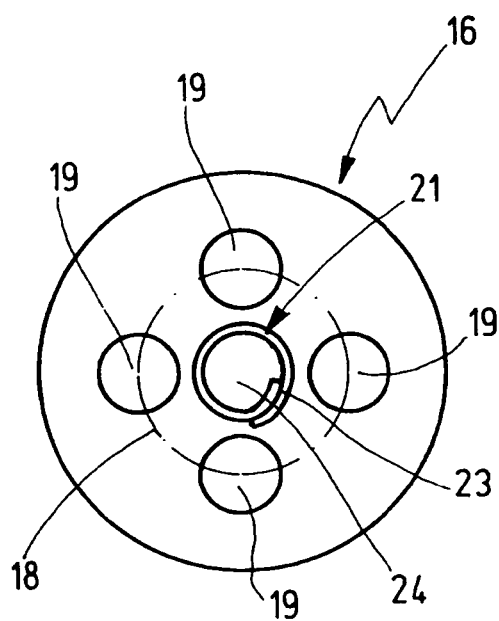

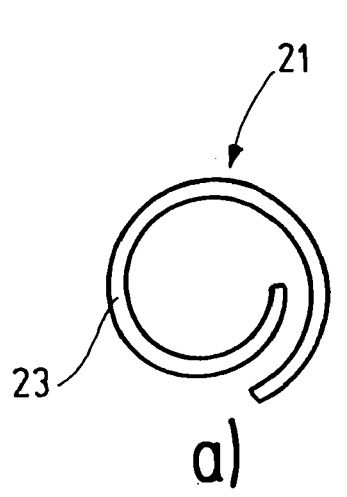
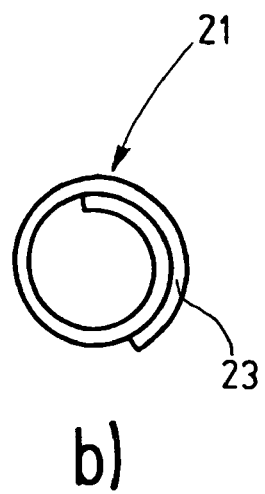
Fig. 6
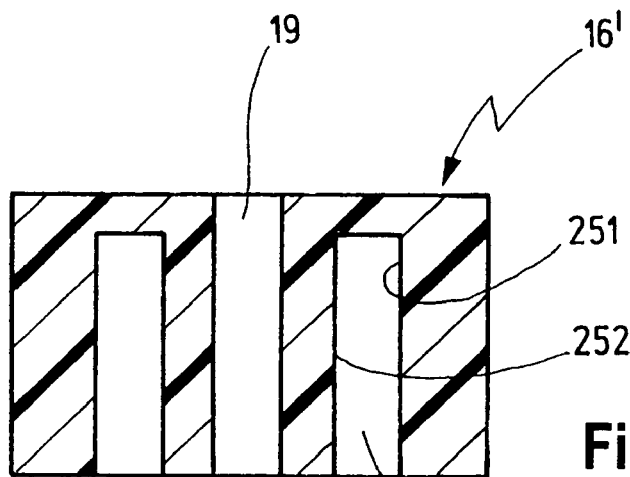
Fig. 7
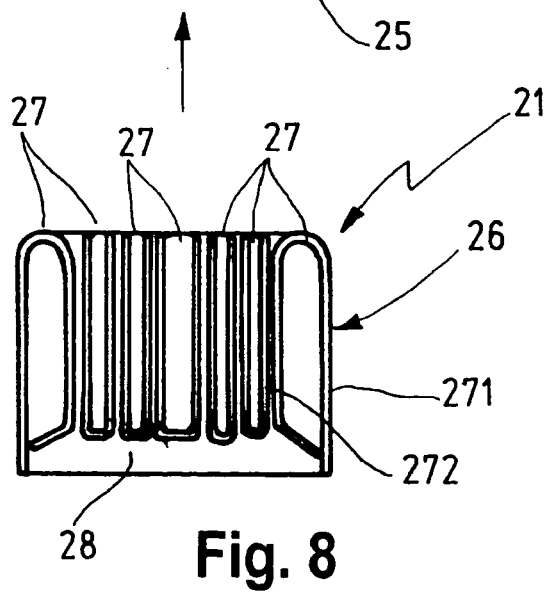
Fig. 8
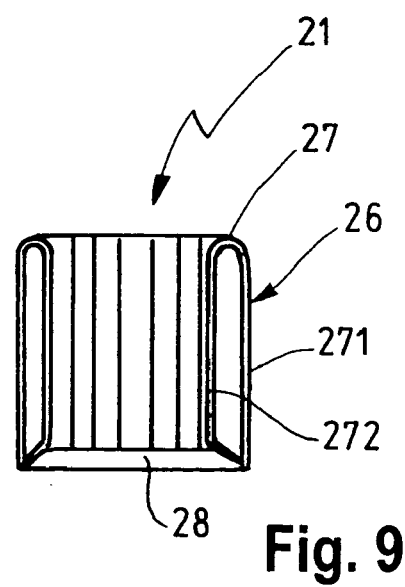
Fig. 9

SENSING ELEMENT FOR DETERMINING A PHYSICAL PROPERTY OF A GAS MIXTURE

FIELD OF THE INVENTION

The present invention relates to a sensing element for determining a physical property of a gas mixture, in particular the exhaust gas of internal combustion engines.

BACKGROUND INFORMATION

Such sensing elements may be designed as gas sensors for determining the concentration of a gas component of a gas mixture, in particular the oxygen concentration in the exhaust gas of an internal combustion engine, or as sensor for measuring the temperature or the pressure of the gas mixture, in particular the temperature or the pressure of the exhaust gas of an internal combustion engine.

In a known gas sensing element, in particular for determining the oxygen concentration of the exhaust gas of internal combustion engines (German Published Patent Application No. 41 26 378), the elastic, plug-type molded piece that is used to feed the connector cable out of the housing in a gas-tight manner is made of a heat-resistant material such as PTFE. However, materials such as silicon rubber or fluorelastomers, for instance FKM or FFKM, are used as well. By radial compression of the molded piece, which is brought about by an all-around tamping of the housing, the molded piece is pressed onto the insulation covering of the cable and then has a sealing effect; the sealing effect may be optimized further by the shape of the axial feed-through hole for the cable and by the surface roughness of the insulation covering of the cable.

Under temperature load, the characteristics of the elastomers exposed to mechanical pressure change in a disadvantageous manner with respect to the sealing effect. Depending on the type of elastomer used, it will soften or harden, the hardening even leading to embrittlement in extreme cases. An adequate sealing effect will then no longer be ensured in all these cases. As a result, in sensing elements where higher thermal demands are made on the cable exit, the use of elastomeric molded pieces has already been abandoned and other measures are taken to seal the cable exit point.

SUMMARY OF THE INVENTION

The sensing element according to the present invention has the advantage that, due to the spring element which is prestressed during installation, the contact pressure of the molded piece on the cable is kept virtually constant even with decreasing elasticity of the molded piece as a result of high temperature stress, so that the sealing effect of the molded piece is maintained in unchanged form. This makes it possible to utilize elastomers as material for the molded piece even at temperatures that are 20–50° C. above the temperature to which the cable exit, which is usually sealed by an elastomeric molded piece, is allowed to be exposed in known sensing elements. The use of elastomers in turn results in considerable cost savings compared to other, high-temperature-resistant cable feed-throughs.

According to an advantageous specific embodiment of the present invention, the molded piece has a blind hole having a circular inner cross section and at least two feed-through holes for each cable, which are preferably arranged equidistantly on a divider circle that is concentric with respect to the blind hole. The molded element is designed as clamping sleeve, which is rolled up in the shape of a helical spring and inserted into the blind hole. When the metallic housing is tamped all-around, the clamping sleeve is prestressed in that the sleeve, while reducing its inner diameter, slides over itself, so that the "helical spring" is tensioned. Due to the tensioned sleeve, the material of the molded piece is pressed against the insulation covering of the cables in a radial manner. If the elasticity of the material decreases, the contact pressure will remain virtually unchanged because of the acting spring force of the clamping sleeve, thereby maintaining the sealing effect of the molded piece.

BRIEF DESCRIPTION OF THE DRAWING

FIG. 2 shows a longitudinal section of a molded piece for the feed-through of a cable in the sensing element according to FIG. 1, including an inserted spring element.

FIG. 3 shows a view of the molded piece in the direction of arrow III in FIG. 2.

FIG. 4 shows a longitudinal section of the molded piece with inserted spring element according to an additional exemplary embodiment.

FIG. 5 shows a view of the molded piece in the direction of arrow V in FIG. 4.

FIG. 6 shows an enlarged plan view of the spring element in the molded piece according to FIGS. 4 and 5 in the untensioned (a) and tensioned (b) state.

FIG. 7 shows a longitudinal section of the form element according to a third exemplary embodiment.

FIG. 8 shows a spring element for insertion into the molded piece according to FIG. 7 in the untensioned state.

FIG. 9 shows the spring element according to FIG. 8 in the tensioned state.

DETAILED DESCRIPTION

Figure 1:
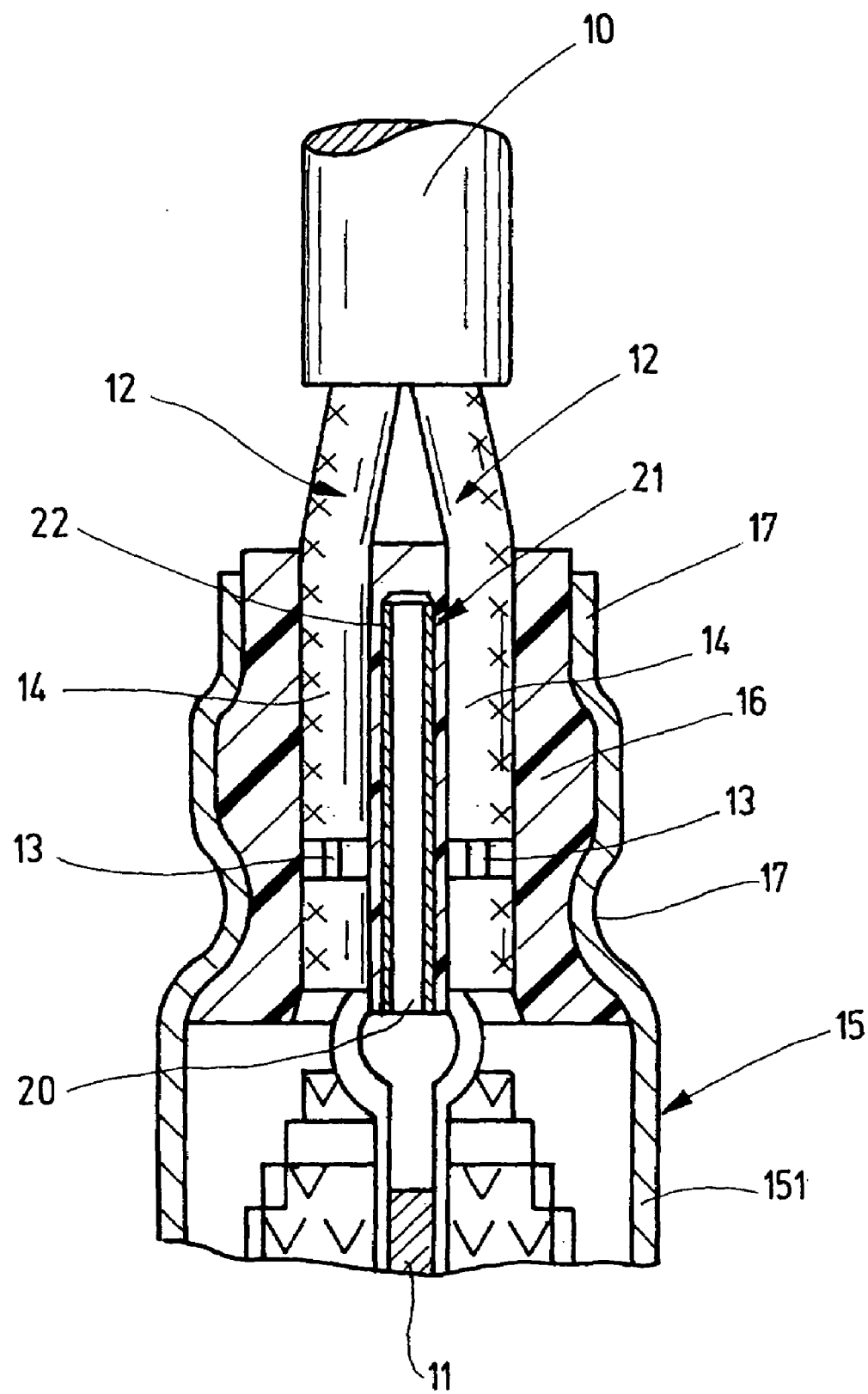
FIG. 1 shows in excerpted form, a longitudinal section of a sensing element for determining a physical property of a gas mixture.

The sensing element—shown in a cut-away view in longitudinal section—for determining a physical property of a gas mixture, for example the oxygen concentration in the exhaust gas of an internal combustion engine, has a sensor element 11 whose one end is exposed to the gas mixture, i.e., the exhaust gas, and at whose other end a contacting of at least one electrical cable 12, via which sensor element 11 is connected to a control unit, takes place. In the exemplary embodiment of FIGS. 1 to 3, a total of four cables is connected, these cables being combined to form a connector cable 10. Each cable 12 has an electrical conductor 13 and a cable insulation 14 surrounding electrical conductor 13.

Sensor element 11 is accommodated in a housing 15, which is made up of a solid metal body (not shown here) and a metallic protective sleeve 151 affixed to the metal body. Sensor element 11 is conducted through the metal body in a gas-tight manner and in its contact region is enclosed with radial clearance by protective sleeve 151, which also extends across a section of cables 12 connected to sensor element 11. For a gas-tight cable feed-through of cables 12 out of housing 15, an elastically deformable, plug-type molded piece 16 is inserted in the end of protective sleeve 151 facing away from the solid metal body, this molded piece 16 enclosing cables 12 in a gas-tight manner by radial compression. Silicon rubber or fluorelastomers are used as material for molded piece 16; the radial tamping is brought about by an all-around compression 17 of metallic protective sleeve 151.

In the exemplary embodiment of FIGS. 1 to 3, molded piece 16 has four feed-through holes 19, which are arranged equidistantly on a divider circle 18 and through which one of the altogether four cables 12 of connector cable 10 is fed in each case. A blind hole 20, which has bulges 201 extending into the spaces between feed-through holes 19 in the manner of a finger, is introduced in molded piece 16, coaxially with respect to divider circle 18. Blind hole 20 is introduced from the front end of molded piece 16, which faces sensor element 11. The number of bulges 201 of blind hole 20 corresponds to the number of feed-through holes 19 arranged on divider circle 18 and presupposes that at least three feed-through holes 19 are provided in molded piece 16. Bulges 201 are shaped such that each extends along two adjacent feed-through holes 19 across an approximately 90° circumferential angle, in parallel to the hole wall of feed-through holes 19, so that each feed-through hole 19 is enclosed by blind hole 20 having bulges 201 across an approximately 180° circumferential angle. In the altogether four feed-through holes 19 provided in molded piece 16 in this case, blind hole 20 therefore has an approximately clover-shaped hole cross-section. Accommodated in blind hole 20, in a form-locking manner, is a spring element 21, which is configured as clamping sleeve 22 having a form that corresponds to the contour of blind hole 20 having bulges 201. Clamping sleeve 22 is made of thin-walled spring steel and composed of a plurality of layers, which are spot-welded to hold them together. The thickness of a layer is less than 0.1 mm, for instance.

During installation of the sensing element, after cables 12 have been guided through feed-through holes 19 and after molded piece 16 has been inserted into the end region of protective sleeve 151, metallic protective sleeve 151 is reduced in diameter by all-around tamping 17 of metallic protective sleeve 151, such tamping being produced, for instance, with the aid of a tool which has stamps that act in the radial direction. In this way spring element 21 situated in blind hole 20 is tensioned, namely by overall compression of clamping sleeve 22, a radial contact pressure of molded piece 16 on cables 12 being generated simultaneously via spring element 21, so that a gas-tight sealing of cables 12 in feed-through holes 19 is ensured. Spring element 21, tensioned during all-around tamping 17, will maintain this contact pressure on a long-term basis even when the elastic property of the material of the molded piece lessens as a result of high temperature stresses.

Molded piece 16, shown in longitudinal section and in a view from below in FIGS. 4 and 5, is identical to molded piece 16 according to FIGS. 2 and 3, so that identical components have been provided with matching reference numerals. In this case spring element 21 is not configured as clamping sleeve having a plurality of radial fingers or bulges, but is designed as clamping sleeve 23 rolled up in the manner of a helical spring, which is likewise inserted into a now circular blind hole 24 in molded piece 16. Drawing a of FIG. 6 shows clamping sleeve 23, rolled up in the manner of a helical spring, in the untensioned state, while drawing b shows it in the tensioned state. Clamping sleeve 23 rolled up in the way of a helical spring is inserted into blind hole 20 with slight prestressing (FIG. 6a). If metallic protective sleeve 151 is then subjected to all-around tamping during the afore-described installation procedure, helical-spring-shaped clamping sleeve 23 is tensioned and assumes the form shown in FIG. 6b, in which it exerts an even radial pressure on the hole walls of blind hole 20. This radial pressure of helical-spring-shaped clamping sleeve 23 provides for a constant contact pressure of the material of the molded piece on cable insulation 14 of cables 12, this being the case even when the elasticity of the molded piece material decreases.

Molded piece 16', shown in FIG. 7 as additional exemplary embodiment in longitudinal section, is suited for the through-feeding of only a single cable 12. Molded piece 16' has a central feed-through hole 19 for cable 12 and an annular groove 25 concentrically surrounding through-feed hole 19, this groove being introduced from the direction of the particular front end of molded piece 16 that will point to the interior of housing 15 once molded piece 16' has been installed, i.e., point toward sensor element 11. Inserted in annular groove 25 is spring element 21 shown in FIG. 8, which is configured as clamping sleeve 26 having a multitude of axially extending spring arms 27, which are held together by a sleeve ring 28. Each spring arm 27 has an outer spring leg 271, which is an integral part of sleeve ring 28, and an inner spring leg 272, which is bent off from outer spring leg 271 at its sleeve-ring-remote end, the inner spring leg being guided back in parallel with outer spring leg 271, up to sleeve ring 28. The mutual clearance between the two spring legs 271, 272 corresponds approximately to the width of annular groove 325. Clamping sleeve 26 is inserted into annular groove 25 in molded piece 16', outer spring legs 271 coming to rest against outer groove wall 251 and inner spring legs coming to rest against inner groove wall 252.

If metallic protective sleeve 15 is then tamped all-around after molded piece 16' has been installed, spring legs 271, 272 are pressed together, their mutual distance being reduced in the process. This tensions clamping sleeve 26 and generates a restoring force acting on inner groove wall 252, which provides for a pressure-tight contacting of the material of the molded piece with respect to cable insulation 14 of cable 12. FIG. 9 shows clamping sleeve 26 tensioned by all-around tamping.

Figure 10:
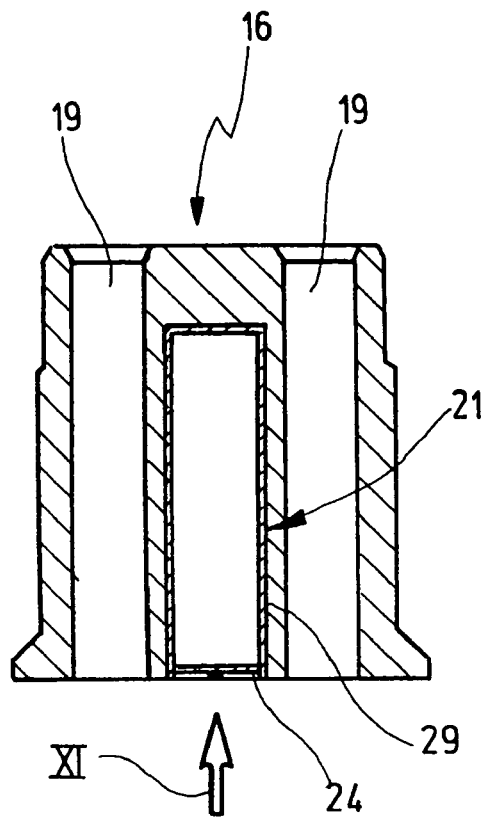
FIG. 10 shows a longitudinal section of the molded piece with inserted spring element according to a fourth exemplary embodiment.
Figure 11:
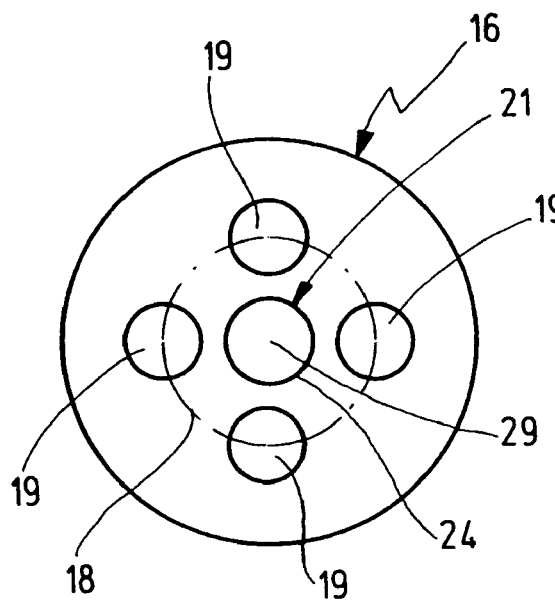
FIG. 11 shows a view of the molded piece in the direction of arrow XI in FIG. 10.

The exemplary embodiment of molded piece 16 introduced in FIGS. 10 and 11 is identical to molded piece 16 according to FIGS. 4 and 5, so that identical components have been provided with matching reference numerals. Here, too, molded piece 16 has a total of four feed-through holes 19 for cables 12, these holes being arranged equidistantly on a divider circle 18, and it also has a central blind hole 24, which is coaxial with respect to divider circle 19. In this case, spring element 21 situated in blind hole 24 is a hollow cylinder 29, which is closed at the front end and encloses an air volume. Hollow cylinder 29 acts as air spring and is pressed together during the all-around tamping performed after molded piece 16 has been installed, so that the air volume is compressed and exerts an even radial pressure on the cylinder walls of hollow cylinder 29. This radial pressure is in turn transmitted to the molded piece material, so that it is pressed against cable insulation 14 of cables 12 in a gas-tight manner.

Figure 12:
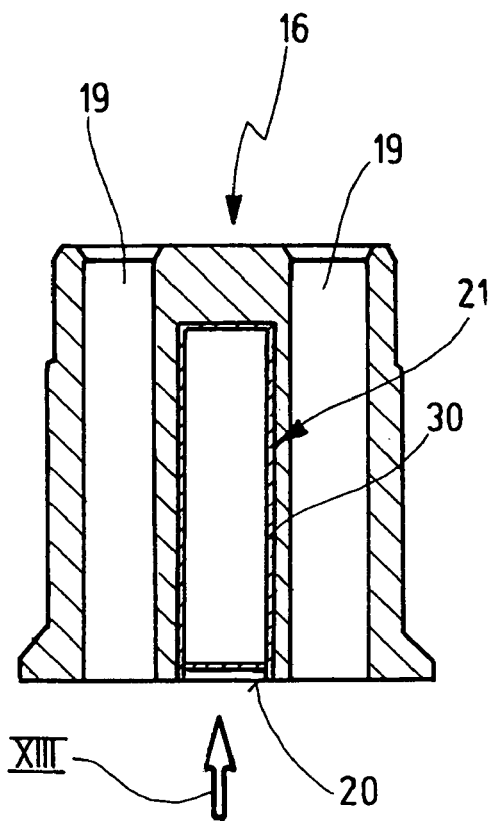
FIG. 12 shows a longitudinal section of the molded piece with inserted spring element according to a fifth exemplary embodiment.
Figure 13:
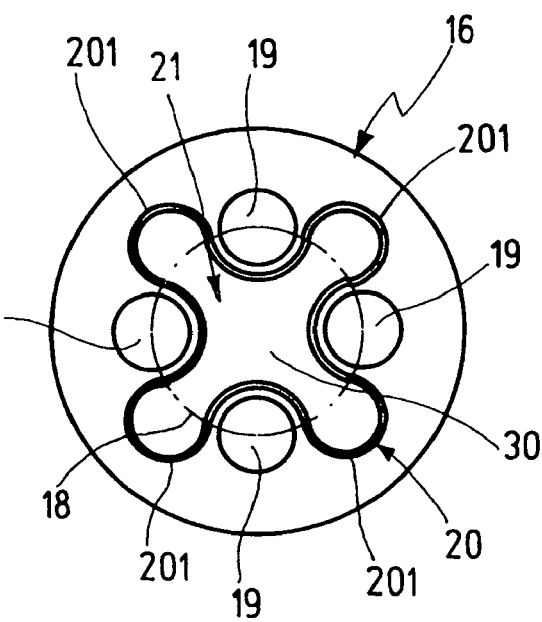
FIG. 13 shows a view of the molded piece in the direction of arrow XIII in FIG. 12.

The exemplary embodiment of molded piece 16 shown in longitudinal section and in a view from below in FIGS. 12 and 13 is identical to molded piece 16 according to FIGS. 2 and 3. Here, too, blind hole 20 has finger-type bulges 201, which extend between feed-through holes 19 arranged equidistantly on a divider circle 18. Inserted in blind hole 20 having finger-type bulges 201 is spring element 21 in the form of a hollow body 30 closed at the front end, whose form is adapted to the contour of blind hole 20 having bulges 201, so that hollow body 30 is lying in blind hole 20 with form-locking. Hollow body 30 in turn encloses an air volume, which is compressed by the radial compression of molded piece 16 resulting from the all-around tamping. In this way, hollow body 30 acts as tensioned air spring having a restoring force, so as to press the material of the molded piece against cables 12 in a radial manner.

What is claimed is:

1. A sensing element for determining a physical property of a gas mixture, comprising:
   a housing;
   at least one electrical cable;
   a sensor element arranged in the housing and connected to the at least one electrical cable;
   a molded piece made of an elastically deformable material and for sealing the housing, the molded piece enclosing the at least one electrical cable in a gas-tight manner by radial compression; and
   a spring element arranged in a blind hole of the molded piece, the spring element being able to be tensioned by the radial compression and in the tensioned state generating a force component that acts on the at least one electrical cable in a radial manner.

2. The sensing element as recited in claim 1, wherein:
   the gas mixture includes an exhaust gas of an internal combustion engine.

3. A sensing element for determining a physical property of a gas mixture, comprising:
   a housing;
   at least one electrical cable;
   a sensor element arranged in the housing and connected to the at least one electrical cable;
   a molded piece made of an elastically deformable material and for sealing the housing, the molded piece enclosing the at least one electrical cable in a gas-tight manner by radial compression; and
   a spring element arranged in the molded piece, the spring element being able to be tensioned by the radial compression and in the tensioned state generating a force component that acts on the at least one electrical cable in a radial manner wherein:
      the molded piece includes a blind hole and at least two feed-through holes, each being designed for the at least one electrical cable and arranged on a divider circle that is concentric with respect to the blind hole, and
      the spring element includes a clamping sleeve that is rolled up as a helical spring and inserted into the blind hole.

4. The sensing element as recited in claim 3, wherein:
   the at least two feed-through holes are arranged equidistantly on the divider circle.

5. A sensing element for determining a physical property of a gas mixture, comprising:
   a housing;
   at least one electrical cable;
   a sensor element arranged in the housing and connected to the at least one electrical cable;
   a molded piece made of an elastically deformable material and for sealing the housing, the molded piece enclosing the at least one electrical cable in a gas-tight manner by radial compression; and
   a spring element arranged in the molded piece, the spring element being able to be tensioned by the radial compression and in the tensioned state generating a force component that acts on the at least one electrical cable in a radial manner, wherein:
      the molded piece includes at least three feed-through holes, each designed for one cable and arranged on a divider circle,
      the molder piece includes a blind hole that is coaxial with respect to the divider circle and includes bulges extending between the at least three feed-through holes in the manner of a finger, and
      the spring element includes a clamping sleeve having a sleeve shape that corresponds to a contour of the blind hole and is accommodated in the blind hole in a form-locking manner.

6. The sensing element as recited in claim 5, wherein:
   the at least three feed-through holes are arranged equidistantly on the divider circle.

7. The sensing element as recited in claim 3, wherein:
   the clamping sleeve includes thin-walled spring steel.

8. The sensing element as recited in claim 7, wherein:
   the clamping sleeve includes a plurality of layers spot-welded to each other.

9. The sensing element as recited in claim 3, wherein:
   the clamping sleeve is inserted into the blind hole with slight prestressing.

10. A sensing element for determining a physical property of a gas mixture, comprising:
    a housing;
    at least one electrical cable;
    a sensor element arranged in the housing and connected to the at least one electrical cable;
    a molded piece made of an elastically deformable material and for sealing the housing, the molded piece enclosing the at least one electrical cable in a gas-tight manner by radial compression; and
    a spring element arranged in the molded piece, the spring element being able to be tensioned by the radial compression and in the tensioned state generating a force component that acts on the at least one electrical cable in a radial manner, wherein:
       the molded piece includes a feed-through hole for the at least one electrical cable and an annular groove concentrically surrounding the feed-through hole, and
       the spring element includes a clamping sleeve having a plurality of axially extending spring arms and is inserted into the annular groove.

11. The sensing element as recited in claim 10, wherein:
    the spring arms each have an outer spring leg integrally formed with a sleeve ring and an inner spring leg, the outer spring leg being bent away from the inner spring leg at a sleeve-ring remote end thereof,
    the inner spring leg is guided back in parallel with the outer spring leg, up to the sleeve ring, and
    a clearance of the outer spring leg and the inner spring leg corresponds roughly to a groove width of the annular groove.

12. The sensing element as recited in claim 1, wherein:
    the molded piece includes a blind hole and at least two feed-through holes, the at least two feed-through holes being designed for the at least one electrical cable and being arranged on a divider circle that is concentric with respect to the blind hole, and the spring element includes a hollow cylinder with an enclosed air volume and is situated in the blind hole in a form-fitting manner.

13. The sensing element as recited in claim 12, wherein:
the at least two feed-through holes are arranged equidistantly on the divider circle.

14. A sensing element for determining a physical property of a gas mixture, comprising:
a housing;
at least one electrical cable;
a sensor element arranged in the housing and connected to the at least one electrical cable;
a molded piece made of an elastically deformable material and for sealing the housing, the molded piece enclosing the at least one electrical cable in a gas-tight manner by radial compression; and
a spring element arranged in the molded piece, the spring element being able to be tensioned by the radial compression and in the tensioned state generating a force component that acts on the at least one electrical cable in a radial manner, wherein:

the molded piece includes:
at least three feed-through holes, each designed for the at least one electrical cable and being arranged on a divider circle, and
a blind hole that is coaxial with respect to the divider circle and includes bulges extending between the at least three feed-through openings in the manner of a finger, and
the spring element includes a hollow body having an enclosed air volume and has a hollow-body form that is adapted to a contour of the blind hole, the spring element being situated in the blind hole in a form-fining manner.

15. The sensing element as recited in claim 14, wherein:
the at least three feed-through holes are arranged equidistantly on the divider circle.

16. The sensing element as recited in claim 1, wherein:
the elastically deformable material includes an elastomer.

* * * * *